United States Patent [19]

Golden et al.

[11] Patent Number: 4,534,350

[45] Date of Patent: Aug. 13, 1985

[54] TWO-PIECE TISSUE FASTENER WITH COMPRESSIBLE LEG STAPLE AND RETAINING RECEIVER

[75] Inventors: Donald M. Golden, Cherry Hill, N.J.; William P. McVay, Clearwater, Fla.

[73] Assignee: Ethicon, Inc., Somerville, N.J.

[21] Appl. No.: 506,082

[22] Filed: Jun. 20, 1983

[51] Int. Cl.³ .............................................. A61B 17/04
[52] U.S. Cl. .......................... 128/334 C; 227/DIG. 1
[58] Field of Search .......... 128/346, 337, 335, 334 R, 128/334 C, 330, 325, 326, 92 B, 335.5; 3/1; 227/DIG. 1, 15–18, 77; 411/469, 451, 360, 501, 506, 362–364, 455–457; 24/543, 518, 614, 623, 703, 297, 150 FP, 16 PB, 697, 580, 581, 584, 453, 30.5 P, 537, 515, 513, 503, 94–96

[56] References Cited

U.S. PATENT DOCUMENTS

| | | |
|---|---|---|
| Re. 27,391 | 6/1972 | Merser .................. 24/150 FP X |
| 306,479 | 10/1884 | Goddard ........................ 24/95 |
| 389,660 | 9/1888 | Mandel et al. .............. 411/457 X |
| 579,831 | 3/1897 | Ketchum ....................... 24/95 |
| 1,988,233 | 1/1935 | Berendt ........................ 24/95 |
| 2,794,981 | 6/1957 | Brayton ....................... 227/15 |
| 2,881,762 | 4/1959 | Lowrie ....................... 128/337 |
| 2,897,561 | 8/1959 | Megibow ....................... 24/95 |
| 2,900,696 | 8/1959 | Bacon ...................... 24/614 X |
| 3,009,852 | 11/1961 | Gruner .................... 128/330 X |
| 3,166,072 | 1/1965 | Sullivan .................. 128/346 X |
| 3,210,820 | 10/1965 | Humiston .................. 24/584 X |
| 3,326,217 | 6/1967 | Kerr ................. 227/DIG. 1 C X |
| 3,357,296 | 12/1967 | Lefever .................. 128/334 C X |
| 3,494,006 | 2/1970 | Brumlik .................. 411/456 X |
| 3,570,497 | 3/1971 | Lemole .................... 128/335.5 |
| 3,577,601 | 5/1971 | Mariani et al. ................. 24/16 |
| 3,683,927 | 8/1972 | Noiles .................... 128/326 X |
| 3,744,495 | 7/1973 | Johnson ..................... 128/330 |
| 3,802,438 | 4/1974 | Wolvek ..................... 128/335 |
| 3,857,396 | 12/1974 | Hardwick .................. 128/335 |
| 3,875,648 | 4/1975 | Bone ...................... 227/19 X |
| 3,981,051 | 9/1976 | Brumlik .................. 411/456 X |
| 4,006,747 | 2/1977 | Kronenthal et al. ......... 128/337 X |
| 4,038,725 | 8/1977 | Keefe ..................... 24/150 FP |
| 4,060,089 | 11/1977 | Noiles .................... 128/337 X |
| 4,235,238 | 11/1980 | Ogiu et al. ............... 128/335 X |
| 4,259,959 | 4/1981 | Walker ..................... 128/337 |
| 4,294,255 | 10/1981 | Geroc .................... 128/334 C |
| 4,326,531 | 4/1982 | Shimonaka .................. 128/326 |
| 4,400,833 | 8/1983 | Kurland ......................... 3/1 |
| 4,402,445 | 9/1983 | Green .................. 128/334 R X |
| 4,454,875 | 6/1984 | Pratt et al. ................. 128/92 B |

FOREIGN PATENT DOCUMENTS

| | | | |
|---|---|---|---|
| 1097171 | 3/1981 | Canada ................... 128/330 |
| 1385691 | 12/1964 | France ..................... 40/300 |
| 8301190 | 4/1983 | Int'l Pat. Inst. .......... 227/DIG. 1 |
| 82738 | 10/1919 | Switzerland ............... 128/330 |
| 972731 | 10/1964 | United Kingdom .......... 128/346 |

Primary Examiner—Michael H. Thaler
Attorney, Agent, or Firm—Robert L. Minier

[57] ABSTRACT

A fastener is provided to hold together portions of mammalian tissue and includes an open loop fastening member and a receiver adapted to receive the legs of the fastening member. Each fastening member leg has two oppositely facing rows of resilient, hemispherical, convex members to cooperate with a bore in the receiver to effect engagement of the fastening member and receiver.

2 Claims, 4 Drawing Figures

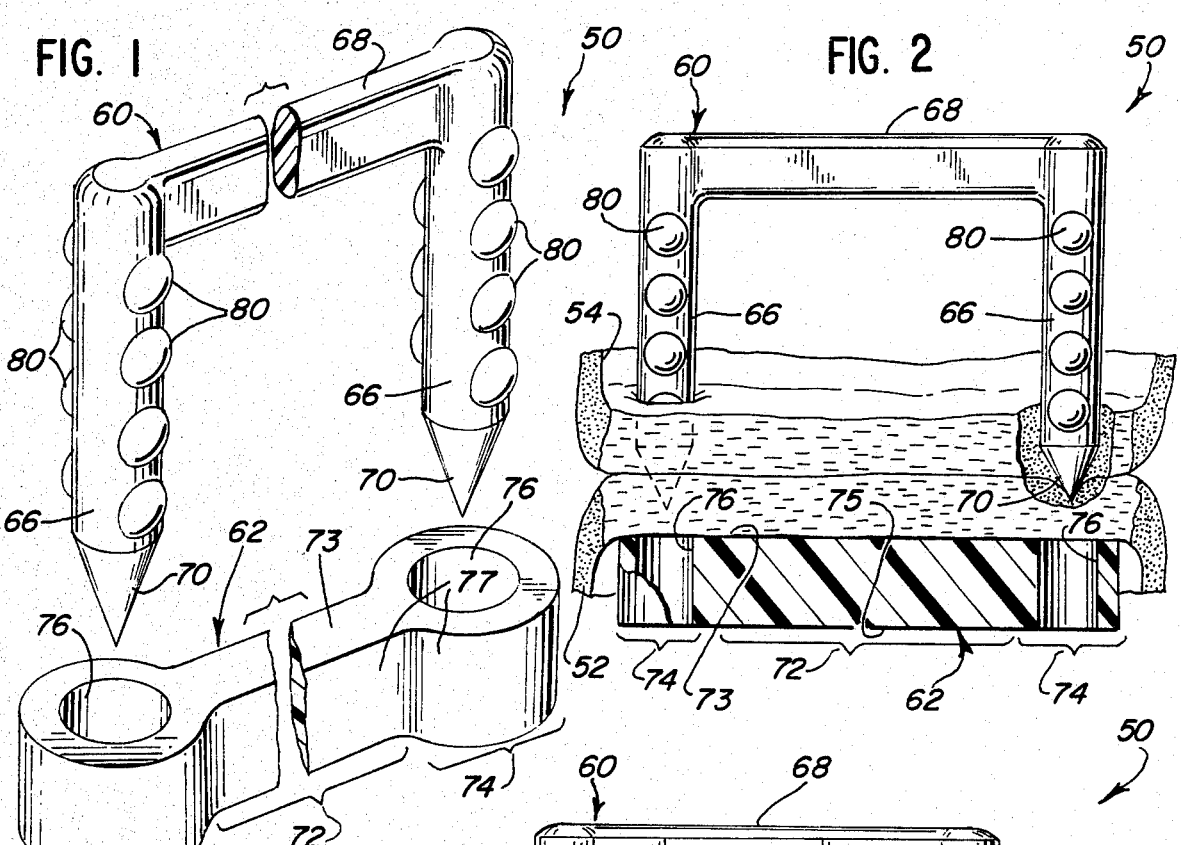
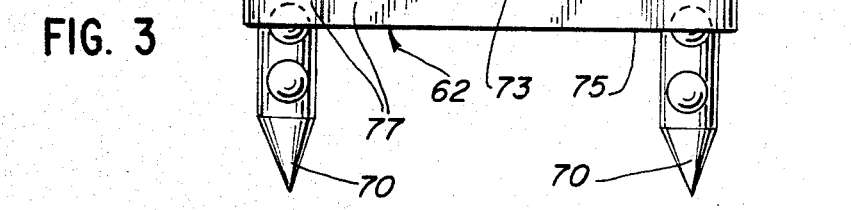
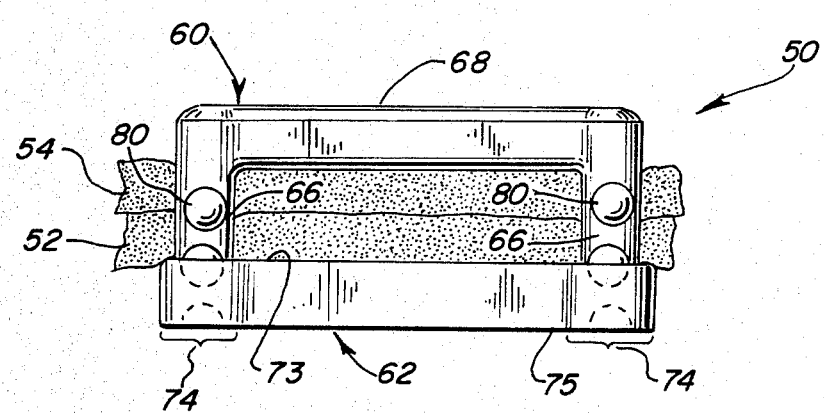

TWO-PIECE TISSUE FASTENER WITH COMPRESSIBLE LEG STAPLE AND RETAINING RECEIVER

DESCRIPTION

1. Technical Field

This invention relates, in general, to the fastening together of portions of tissue in surgical procedures.

2. Background of the Invention

In various surgical procedures, fasteners in the form of staples or the like are employed for holding tissue portions together to facilitate healing of a wound or incision. For example, a locking staple, having a tongue and groove structure by which the staple is locked, is disclosed in U.S. Pat. No. 2,881,762. A metal staple especially adapted for ligating blood vessels is disclosed in U.S. Pat. No. 3,079,608. International Patent Application No. PCT/SU79/00049 discloses a variety of fastening devices and instruments for performing circular anastomoses on the large intestine. The aforementioned disclosures serve as examples of a wide variety of tissue fastening devices and techniques that may be employed in general and/or specific surgical situations.

One common type of fastening device for joining or holding together soft tissue portions is the generally "U"-shaped staple which is typically fabricated from a suitable metal. Such staples, although generally described as having two legs joined to define a "U"-shape when unclinched, may also be regarded as having a configuration of an "open" loop when unclinched. The legs need not necessarily be parallel but are typically adapted for penetrating the tissue portions and for receiving between them some of the tissue material.

Other examples of U-shaped or open loop staples, as well as of methods and instruments for applying such staples to tissue, are disclosed in U.S. Pat. Nos. 3,252,643, 3,482,428, 3,692,224, 3,790,057, 3,795,034, 3,889,683, 4,198,982, 4,316,468, and 4,319,576.

Other tissue fastening devices have been proposed and differ from staples per se in that these other devices may have a plurality of components and do not have to be clinched in the manner used to set a staple. One such device is disclosed in U.S. Pat. No. 4,060,089 and includes a fastener strip provided with a plurality of longitudinally spaced, parallel prongs which are adapted to penetrate two overlapped tissue portions from one side so that the distal ends of the prongs project from the other side of the tissue portions.

The fastener device further includes a retainer strip which is adapted to be placed on the other side of the tissue portions opposite the fastener strip to engage the ends of the projecting fastener strip prongs and thus secure the tissue portions tightly between the fastener strip and the retainer strip. The retainer strip defines frustoconical openings for receiving the fastener strip prongs which each include a plurality of spaced-apart, frustoconical engaging members for engaging the retainer strip at a desired position relative to the prongs. This provides for the capability of adjusting the distance between the fastener strip and the retainer strip. Such a fastening device may be fabricated from a biodegradable or absorbable material.

Yet another tissue fastening device having a plurality of components is disclosed in co-pending commonly assigned U.S patent application U.S.S.N. 349,433, filed Mar. 18, 1982. The fasteners disclosed in that application are made from various polymeric materials and the legs of the U-shaped staple portion of the fastener have a taper to improve the penetration of the staple into tissue Although many of the above-discussed types of tissue fastening devices and techniques are satisfactory in various applications, there is a need to provide an improved fastening device, especially one completely fabricated from absorbable materials.

Also, it would be desirable to provide an improved fastening device fabricated from absorbable materials that can provide primary approximation of the tissue edges to insure that the tissue edges are in continuous contact. Further, such an improved fastener should provide a desired amount of hemostatic compression to minimize bleeding, but allow some collateral blood circulation to the wound or incision edges of the tissue to promote healing In addition, such an improved fastener should have the capability to accommodate varying tissue thicknesses and should leave as little tissue cuff or margin as possible in effecting the joining of the tissue.

Further, it would be beneficial if such an improved fastener had a configuration that would enable the fastener to be fabricated with as small a size as possible to minimize dosage. Also, another desirable feature of such an improved fastener would be a fastener configuration that minimizes the possible sites of formation of pockets of infection in the tissue.

Further, such an improved fastener would desirably provide the surgeon with tactile feedback and compensating control during the application of the fastener.

Finally, such an improved fastener should have the capability for maintaining the tissue portions in approximation and compression for a minimum of 21 days in vivo.

It would also be advantageous to provide such a fastener with a design that would facilitate its application to the tissue portions with a simple yet effective method. It would also be desirable if the improved fastener could readily accommodate application by means of an appropriately designed instrument.

SUMMARY OF THE INVENTION

An improved fastener is provided to hold together portions of mammalian tissue, such as are defined by a wound or incision, to facilitate healing of the wound or incision. The fastener comprises an open loop fastening member which has a pair of legs adapted to penetrate two overlapped tissue portions and which has a link connecting the legs. The link is adapted to lie substantially against one of the tissue portions.

Each leg has on its exterior, along at least a portion of its length, a plurality of resilient protuberances. The resilient protuberances each define an increased cross-section region presenting a three dimensionally curved engaging surface along the leg between reduced cross-section regions.

A receiver is provided for being disposed against the other of the tissue portions opposite the fastening member and has means for receiving the fastening member legs after the legs have been inserted through the tissue portions. The receiver has two leg receiving members each defining at least one passage. Each passage has an axial cross section dimension greater than the corresponding reduced cross section region dimension of the leg to be inserted therein but smaller than the corresponding increased cross-section region dimension of the leg to be inserted therein. When the legs are inserted into the receiving members, the protuberances deform to accommodate the insertion and provide an interference friction fit to retain the fastening member and receiver in a selected relative position.

To join the tissue portions with the fastener, the two tissue portions are first approximated in a generally face-to-face relationship. Next, the fastening member is positioned on one side of the tissue portions with the legs oriented at an appropriate angle to penetrate the tissue portions. The receiver is positioned on the other side of the tissue portions opposite the fastening member and generally in alignment with the fastening member legs.

Relative movement is then effected between the fastening member on the one hand and the tissue portions and receiver on the other hand to cause penetration of the tissue portions by the fastening member legs and to cause a portion of each of the fastening member legs to be received within the receiver. The relative movement is effected until the link is disposed against the surface of one of the tissue portions and until the receiver is disposed against the other of the tissue portions. At this point, the leg protuberances of the fastening member have engaged the receiver and prevent separation of the fastening member and receiver.

Numerous other features of various embodiments of a novel tissue fastener will be apparent from the following detailed description and accompanying drawings.

BRIEF DESCRIPTION OF THE DRAWINGS

In the accompanying drawings forming part of the specification, and in which like numerals are employed to desginate like parts throughout the same.

FIG. 1 is a perspective view of a first embodiment of the fastener of the present invention which includes a fastening member and receiver;

FIG. 2 is a fragmentary, partial cross-sectional view of two portions of mammalian tissue defined by an incision or wound with some of the tissue cut away to better show interior detail and illustrating (1) the fastening member of FIG. 1 being inserted into the two portions of the tissue and (2) the receiver of FIG. 1 being held against the tissue portions by suitable means (not illustrated);

FIG. 3 is a view similar to FIG. 2 but showing the fastening member and receiver fully engaged; and FIG. 4 is a view similar to FIG. 3 but showing the fully engaged fastener after the projecting leg portions have been severed

DESCRIPTION OF THE PREFERRED EMBODIMENT

This invention may be used in many different forms. The specification and accompanying drawings disclose only one specific form as an example of the use of the invention. The precise shapes and sizes of the components herein described are not essential to the invention unless otherwise indicated. The invention is not intended to be limited to the embodiment illustrated, and the scope of the invention will be pointed out in the appended claims.

A preferred embodiment of the fastener is illustrated in FIGS. 1-4 and is designated generally therein by reference numeral 50. The fastener 50 is illustrated in FIGS. 3 and 4 in the fully assembled, "set" configuration wherein it is shown holding together two portions 52 and 54 of mammalian tissue, such as are defined by a wound or incision, to facilitate healing of the wound or incision. Typically, a plurality of such fasteners 50 would be used to close a wound or incision. However, with just a small wound or incision, one fastener 50 may be sufficient.

The fastener 50 includes two components, a generally U-shaped or open loop fastening member 60 and a receiver 62, which are initially separated as illustrated in FIG. 1 and which are adapted to cooperate to compress or hold between them the tissue portions.

As is best illustrated in FIGS. 1 and 2, the fastening member 60 includes (1) a pair of legs 66 adapted to penetrate the tissue portions and (2) a link 68 which is connected to the legs 66 and which is adapted to lie substantially against one of the tissue portions (e.g., tissue portion 54 in FIG. 3). The legs 66 of the fastening member are generally parallel to each other and are generally perpendicular to the link 68. Preferably, each leg 66 has a solid, generally cylindrical configuration with a conical end 70 to facilitate or aid in the penetration of the tissue portions The link 68 may have the shape of a regular parallelpiped (as illustrated) or may have any other suitable shape.

Each leg 66 defines on its exterior along at least a portion of its length a plurality of a resilient protuberances, such as convex, hemispherical members 80. Each member 80 defines an increased cross-section region presenting a three dimensionally curved engaging surface between reduced cross-section regions along each leg 66. Preferably, the convex members 80 are arranged in two rows spaced 180 degrees apart on each leg. Also, the convex members 80 are preferably spaced apart and are separated by cylindrical cross-section regions of the leg. Preferably, each convex member 80 in one row on a leg is in longitudinal registry along that leg with a convex member in the other row on that leg.

Each member 80 is generally elastically deformable or compressible when a sufficient force is applied to the exterior of the member 80. Sufficient application of force will cause the member 80 to at least temporarily deform inwardly as long as the force remains applied. The construction and composition of each member 80 is such that when the force is removed, the member 80 returns from the deformed position to its original undeformed, hemispherical shape as illustrated in FIG. 1.

As best illustrated in FIGS. 1 and 2, the receiver 62 includes a central member 72 joining a pair of leg receiving members 74. Each receiving member 74 has a first side 73 (FIG. 1) adapted to be disposed against a tissue portion (tissue portion 52 shown in FIGS. 2 and 3). Each receiving member 74 also has a second side 75 (FIG. 2) facing generally away from the first side 73. Each receiving member 74 also includes an exterior peripheral surface 77 (FIG. 3) extending between the first side 73 and the second side 75.

Each receiving member 74 defines a passage, such as bore 76 (FIGS. 1 and 2), extending from the first side 73 of the receiving member to the second side 75 of the receiving member. Each bore 76 functions to receive one of the fastening member legs 66 after the legs have been inserted through the tissue portions.

Each bore 76 has an axial cross-section dimension greater than the corresponding reduced cross-section region dimension of the leg to be inserted therein but smaller than the corresponding increased cross-section region dimension of the leg to be inserted therein. In other words, in the preferred embodiment illustrated, the bore 76 has a diameter greater than the cylindrical cross-section region of the legs 66 but smaller than the corresponding increased cross-section regions of the legs which are defined by the convex, hemispherical members 80. Thus, when the legs 66 are inserted in the receiving members 74, the convex members 80 deform to accommodate the insertion and provide an interference friction fit which retains the fastening member 60 and receiver 62 in a selected relative position.

The fastening member 60 and receiver 62 may be formed from suitable materials, such as thermoplastic polymer materials that are absorbable by mammalian tissue. For example, the fastening member and receiver may be molded from absorbable polymers or copolymers of poly-dioxanone, lactide, glycolide and the like. The fastener may also be molded from a combination of both such materials.

The fastener 50 is used to join the tissue portions 52 and 54 (FIGS. 2 and 3) in a novel manner. Specifically, the tissue portions 52 and 54 are first approximated in surface-to-surface relationship as best illustrated in FIG. 2. Then the fastening member 60 is positioned on one side of the tissue portions with the legs 66 oriented at an appropriate angle to penetrate the tissue portions. The receiver 62 is held on the other side of the tissue portions opposite the fastening member 60 and generally in alignment with the fastening member legs 66. Specifically, the bores 76 are aligned with the fastening member legs 66.

Next, relative movement between the fastening member 60 and the receiver 62 is effected to urge the fastening member and the receiver closer together to cause the fastening member legs 66 to penetrate the tissue portions 52 and 54 and to locate at least portions of the fastening member legs 66 within the receiver 62. The relative movement between the fastening member 60 and the receiver 62 is terminated when the fastening member link 68 is at a desired distance from the receiver 62 to secure the tissue portions together. Preferably, this movement is terminated after the tissue portions have been compressed together a desired amount.

As the fastening member legs 66 are pushed through the receiving members 74 of the receiver 62, the convex members 80 on the legs engage the receiver in the bores 76. The members 80 are temporarily and elastically deformed to facilitate passage through the receiver.

When the tissue portions 54 and 52 have been compressed the desired amount, the applied forces effecting the relative movement between the fastening member 60 and the receiver 62 are removed. Then the fastening member 60 and the receiver 62 tend to be forced apart by the compressed tissues and this may effect a small, reverse relative movement. However, this small, reverse movement, should it occur, is limited.

When the relative positions of the fastening member 60 and receiver 62 are as illustrated in FIG. 3, at least one convex member 80 on each leg 66 frictionally engages the receiver 62. The frictional engagement prevents withdrawal of the leg 66 from the receiver 62 under the influence of the compressed tissue portions. If the largest part of the convex member 80 is not engaged with the receiver 62, then some small reverse movement may occur until a larger part of the member 80 engages the receiver and terminates further movement.

The distal ends of the fastening member legs 66 will typically protrude from the receiver 62 opposite the side of the receiver that is contacting one of the tissue portions. If desired, the protruding ends of the legs 66 may be severed flush with the bottom of the receiver 62 by a suitable means to provide a smooth bottom structure as illustrated in FIG. 4. Preferably, during the step of severing the protruding portions of the fastening member legs 66, the protruding portions of the fastening member legs are surrounded with a suitable container for catching the leg protruding portions after they are severed so as to prevent the severed portions of the legs from falling into the surrounding tissue or body cavity.

The above-described method for applying the fastener 50 to the tissue portions 52 and 54 may be effected with a suitable instrument specifically designed for holding the fastening member 60 and receiver 62 and for driving the fastening member 60 through the tissue portions and into engagement with the receiver 62. Such an instrument (not illustrated) may include a pair of pivotally mounted jaws with one of the jaws adapted for holding the receiver 62 on one side of the tissue portions and with the other of the jaws adapted for holding the fastening member 60 on the other side of the tissue portions. A suitable driving member may be provided as part of the instrument for driving the fastening member 60 out of its holding jaw, into the tissue portions, and finally into engagement with the receiver 62.

The instrument may include a suitable mechanism for severing the protruding portions of the fastening member legs 66 after the fastening member 60 and receiver 62 have been locked together with the tissue portions under the desired amount of compression. It is to be realized that such an instrument might be preferably provided with means for applying a plurality of such fasteners simultaneously.

ALTERNATIVE DESIGN FEATURES

In the figures, the two legs of the fastening member are connected by a portion of the fastening member (e.g., the link or clamping member) which is illustrated as being generally straight and extending perpendicular to the two legs. The structure need not be limited to such a shape however. Instead, all or a portion of the length of the fastening member between the two legs may be arched or arcuate or may include an arcuate portion (e.g., an inverted U-shaped configuration). This would function to initially provide a free space between the upper tissue portion and the top of the fastening member to allow for some expansion of the tissue.

However, in those situations where increased initial tissue compression is desired, a modified receiver structure may be provided to cooperate with the above-described arcuate fastening member. Specifically, the receiver need not have a flat upper surface as illustrated. Rather, the upper surface of the receiver may be arcuate (e.g., convex) so as to generally match or correspond with the arcuate shape of the fastening member. This can result in an increased compression of the two tissue portions between the receiver and fastening member.

From the foregoing, it will be observed that numerous variations and modifications may be effected without departing from the true spirt and scope of the novel concept of the invention. It is to be understood that no limitation with respect to the specific articles, instruments, and methods illustrated herein is intended or should be inferred. It is, of course, intended to cover by the appended claims all such modifications as fall within the scope of the claims.

What is claimed is:

1. A fastener adapted to hold together two portions of mammalian tissue, such as are defined by a wound or incision, to facilitate healing of the wound or incision, said fastener comprising:

a generally U-shaped fastening member, said fastening member comprising a pair of generally conical distal ends adapted to penetrate said tissue portions and a link normal to, extending between, and connecting said legs; said link being adapted to lie substantially against one of said tissue portions; each said leg being generally cylindrical and having on its exterior along at least a portion of its length two rows of resilient convex members, each convex member defining an increased cross section region presenting a three dimensionally curved engaging surface separated from adjacent members by cylindrical cross section regions of said leg, each row of convex members on a leg being oriented about 180 degrees from the other row on that leg and each convex member in one row on the leg being in longitudinal registry along the leg with a convex member in the other row on that leg; and a receiver having a first leg receiving member for receiving one of said fastening member legs after said legs have been inserted through said tissue portions and having a second leg receiving member for receiving the other of said fastening member legs after said legs have been inserted through said tissue portions; said receiver having a first side adapted to be disposed against the other of said tissue portions; said receiver having a second side facing generally away from said first side; said receiver having an exterior peripheral surface extending between said first and second sides; each said receiving member defining a bore extending from said receiver first side to said receiver second side; each said bore having a substantially uniform diameter, said diameter being greater than the cylindrical cross section regions of the leg to be inserted therein but smaller than the corresponding increased cross section regions of the leg to be inserted therein whereby, when the leg is inserted into said receiving member, said convex members deform to accommodate the insertion and provide an interference friction fit to retain the fastening member and receiver in a selected relative position.

2. The fastener in accordance with claim 1 in which said fastening member is molded from an absorbable thermoplastic polymer and in which said receiver is molded from an absorbable thermoplastic polymer.

* * * * *